(12) United States Patent
Windheuser et al.

(10) Patent No.: US 6,582,401 B1
(45) Date of Patent: Jun. 24, 2003

(54) MULTI-SIZE CONVERTIBLE CATHETER

(75) Inventors: James E. Windheuser, Hopkinton, MA (US); Fernando Alvarez de Toledo, Concord, MA (US)

(73) Assignee: SciMed Life Sytems, Inc., Maple Grove, MN (US)

( * ) Notice: Subject to any disclaimer, the term of this patent is extended or adjusted under 35 U.S.C. 154(b) by 0 days.

(21) Appl. No.: 09/472,582

(22) Filed: Dec. 27, 1999

Related U.S. Application Data

(63) Continuation-in-part of application No. 08/926,200, filed on Sep. 9, 1997, now Pat. No. 6,007,522.
(60) Provisional application No. 60/025,235, filed on Sep. 13, 1996.

(51) Int. Cl.[7] .......................... A61M 5/178; A61M 25/00
(52) U.S. Cl. .................................. 604/164.05; 604/523
(58) Field of Search ........................... 604/506, 164.01, 604/164.05, 164.09, 164.11, 523

(56) References Cited

U.S. PATENT DOCUMENTS

| | | |
|---|---|---|
| 1,204,053 A | 11/1916 | Moore |
| 2,623,520 A | 12/1952 | Bamford, Jr. et al. ...... 128/221 |

(List continued on next page.)

FOREIGN PATENT DOCUMENTS

| | | |
|---|---|---|
| DE | 41 15 007 A1 | 11/1992 |
| EP | 0 328 760 A2 | 8/1989 |
| EP | 0 388 112 A2 | 9/1990 |
| EP | 0 792 657 A2 | 9/1997 |
| EP | 801 955 B1 | 3/1999 |
| WO | WO 92/03963 | 3/1992 |
| WO | WO 96/33764 | 10/1996 |
| WO | WO 98/10820 | 3/1998 |
| WO | WO 98/10821 | 3/1998 |

OTHER PUBLICATIONS

Knecht, Gregory L., M.D. et al., "Double–Channel Fistulotome For Endoscopic Drainage of Pancreatic Pseudocyst", *Gastrointestinal Endoscopy*, vol. 37, No. 3, May/Jun. 1991, pp. 356–357.

Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438–440.

*Primary Examiner*—Sharon Kennedy
(74) *Attorney, Agent, or Firm*—Crompton, Seager & Tufte, LLC

(57) ABSTRACT

The present invention relates to a multi-size catheter for use in biliary endoscopic procedures. The multi-size catheter comprises an outer diameter defined by a plurality of superimposed peelable layers. The peelable layers allow the multi-size catheter to function as a single operator exchange catheter without the need, and additional expense, of an endoscope sheath. Before positioning the multi-size catheter within the working channel of an endoscope, the peelable layers may be selectively removed in order to obtain an outer diameter for the catheter that is less than, but approximate to, the inner diameter of the working channel of the endoscope. The resulting fit eliminates the potential for a guidewire to slip out of the guidewire channel and become pinched between the catheter and the endoscope working channel. With an incorrect fit, a pinched guidewire would restrict the desired movements of both the guidewire and the catheter.

30 Claims, 13 Drawing Sheets

U.S. PATENT DOCUMENTS

| | | | |
|---|---|---|---|
| 3,015,869 A | 1/1962 | Rapata | 24/213 |
| 3,536,281 A | 10/1970 | Meehan et al. | 248/73 |
| 4,345,606 A | 8/1982 | Littleford | 128/784 |
| 4,411,654 A | 10/1983 | Boarini et al. | 604/165 |
| 4,412,832 A | 11/1983 | Kling et al. | 604/164 |
| RE31,855 E | 3/1985 | Osborne | 604/161 |
| 4,696,668 A | 9/1987 | Wilcox | 604/28 |
| 4,748,982 A | 6/1988 | Horzewski et al. | 128/344 |
| 4,762,129 A | 8/1988 | Bonzel | 128/344 |
| 4,771,777 A | 9/1988 | Horzewski et al. | 128/344 |
| 4,781,677 A | 11/1988 | Wilcox | 604/28 |
| 4,835,824 A | 6/1989 | Durham et al. | 24/339 |
| 4,844,092 A | 7/1989 | Rydell et al. | 128/772 |
| 4,900,184 A | 2/1990 | Cleveland | 403/397 |
| 4,905,667 A | 3/1990 | Foerster et al. | 128/4 |
| 4,917,103 A | 4/1990 | Gambale et al. | 128/772 |
| 4,927,418 A | 5/1990 | Dake et al. | 604/264 |
| 4,928,693 A | 5/1990 | Goodin et al. | 128/637 |
| 4,932,413 A | 6/1990 | Shockey et al. | 128/657 |
| 4,946,443 A | 8/1990 | Hauser et al. | 604/165 |
| 4,983,168 A | 1/1991 | Moorehead | 604/161 |
| 4,988,356 A | 1/1991 | Crittenden et al. | 606/192 |
| 4,997,421 A | 3/1991 | Palsrok et al. | 604/174 |
| 4,762,129 A | 7/1991 | Bonzel | |
| 5,040,548 A | 8/1991 | Yock | 128/898 |
| 5,061,273 A | 10/1991 | Yock | 606/194 |
| 5,064,414 A | 11/1991 | Revane | 604/165 |
| 5,125,915 A | 6/1992 | Berry et al. | 604/283 |
| 5,135,535 A | 8/1992 | Kramer | 606/194 |
| 5,147,377 A | 9/1992 | Sahota | 606/194 |
| 5,158,545 A | 10/1992 | Trudell et al. | 604/53 |
| 5,167,634 A | 12/1992 | Corrigan, Jr. et al. | 604/160 |
| 5,195,978 A | 3/1993 | Schiffer | 604/161 |
| 5,205,822 A | 4/1993 | Johnson et al. | 604/96 |
| 5,232,445 A | 8/1993 | Bonzel | 604/96 |
| 5,248,306 A | 9/1993 | Clark et al. | 604/283 |
| 5,250,033 A | 10/1993 | Evans et al. | 604/160 |
| 5,279,562 A | 1/1994 | Sirhan et al. | 604/96 |
| 5,282,479 A | 2/1994 | Havran | 128/772 |
| 5,290,232 A | 3/1994 | Johnson et al. | 604/96 |
| 5,290,241 A | 3/1994 | Kraus et al. | 604/161 |
| 5,300,085 A | 4/1994 | Yock | 606/191 |
| 5,306,247 A | 4/1994 | Pfenninger | 604/96 |
| 5,308,318 A | 5/1994 | Plassche, Jr. | 604/54 |
| 5,320,602 A | 6/1994 | Karpiel | 604/54 |
| 5,324,259 A | 6/1994 | Taylor et al. | 604/96 |
| 5,324,269 A | 6/1994 | Miraki | 604/160 |
| 5,334,143 A | 8/1994 | Carroll | 604/54 |
| 5,334,187 A | 8/1994 | Fischell et al. | 604/194 |
| 5,350,395 A | 9/1994 | Yock | 606/194 |
| 5,364,355 A | 11/1994 | Alden et al. | 604/96 |
| 5,364,376 A | 11/1994 | Horzewski et al. | 604/280 |
| 5,370,623 A | 12/1994 | Kreamer | 604/165 |
| 5,389,087 A | 2/1995 | Miraki | 604/247 |
| 5,397,302 A | 3/1995 | Weaver et al. | 604/54 |
| 5,451,233 A | 9/1995 | Yock | 606/194 |
| 5,454,790 A | 10/1995 | Dubrul | 604/104 |
| 5,458,584 A | 10/1995 | Ginn et al. | 604/280 |
| 5,458,605 A | 10/1995 | Klemm | 606/108 |
| 5,480,389 A | 1/1996 | McWha et al. | 604/165 |
| 5,489,271 A | 2/1996 | Andersen | 604/102 |
| 5,490,837 A | 2/1996 | Blaeser et al. | 604/96 |
| 5,496,346 A | 3/1996 | Horzewski et al. | 606/154 |
| 5,501,227 A | 3/1996 | Yock | 128/662.06 |
| 5,531,700 A | 7/1996 | Moore et al. | 604/164 |
| 5,536,248 A | 7/1996 | Weaver et al. | 604/54 |
| 5,540,236 A | 7/1996 | Ginn | 128/772 |
| 5,599,299 A | 2/1997 | Weaver et al. | 604/54 |
| 5,599,300 A | 2/1997 | Weaver et al. | 604/54 |
| 5,626,600 A | 5/1997 | Horzewski et al. | 606/194 |
| 5,706,827 A | 1/1998 | Ehr et al. | 128/772 |
| 5,725,504 A | 3/1998 | Collins | 604/165 |
| 5,788,681 A | 8/1998 | Weaver et al. | 604/280 |
| 5,800,414 A | 9/1998 | Cazal | 604/280 |
| 5,833,706 A | 11/1998 | St. Germain et al. | 606/194 |
| 5,843,028 A | 12/1998 | Weaver et al. | 604/54 |
| 5,849,016 A | 12/1998 | Suhr | 606/108 |
| 5,921,971 A | 7/1999 | Agro et al. | 604/280 |
| 6,007,522 A | 12/1999 | Agro et al. | 604/264 |
| 6,096,009 A | 8/2000 | Windheuser et al. | 604/165 |
| 6,152,910 A | 11/2000 | Agro et al. | 604/523 |

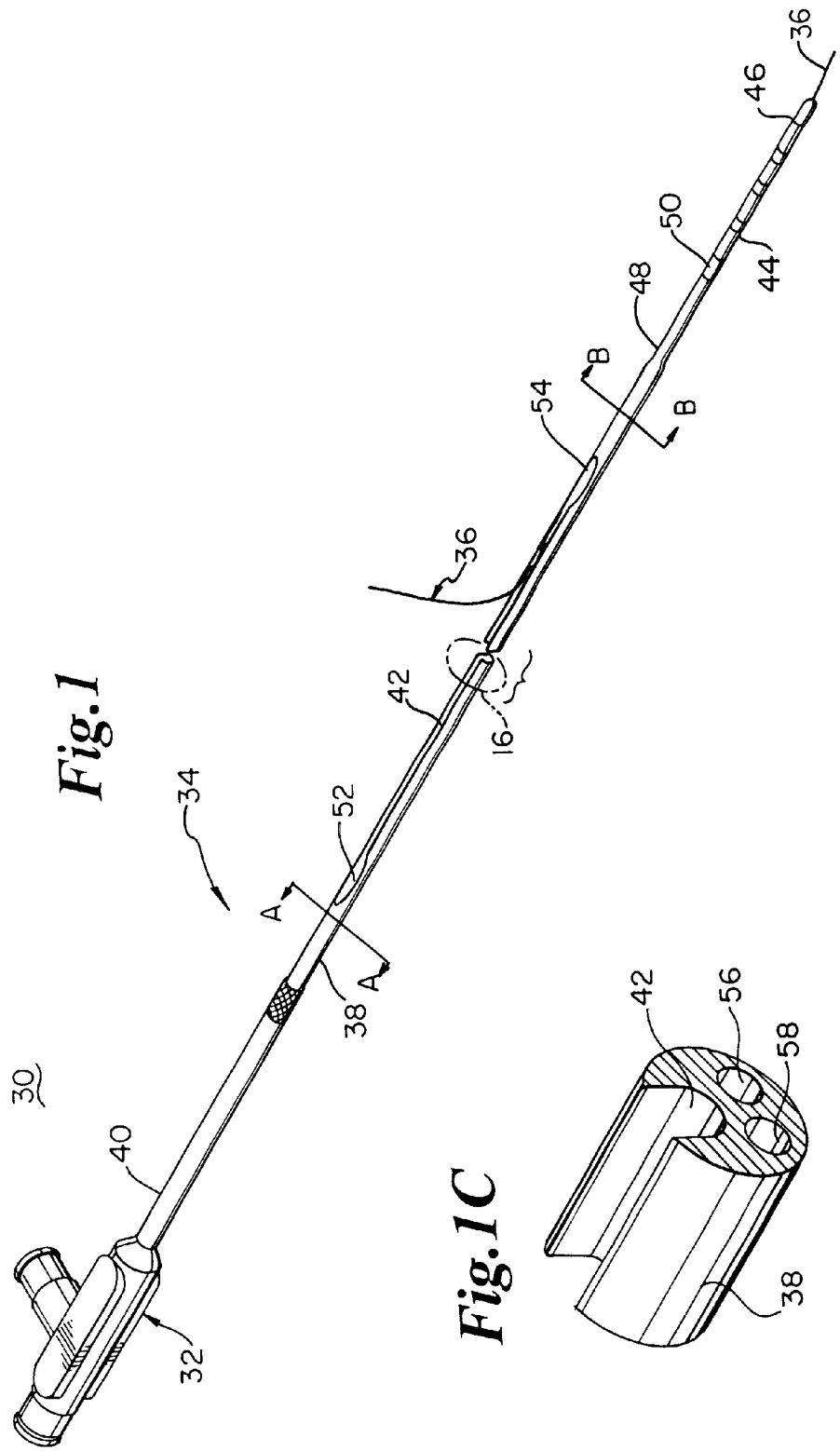

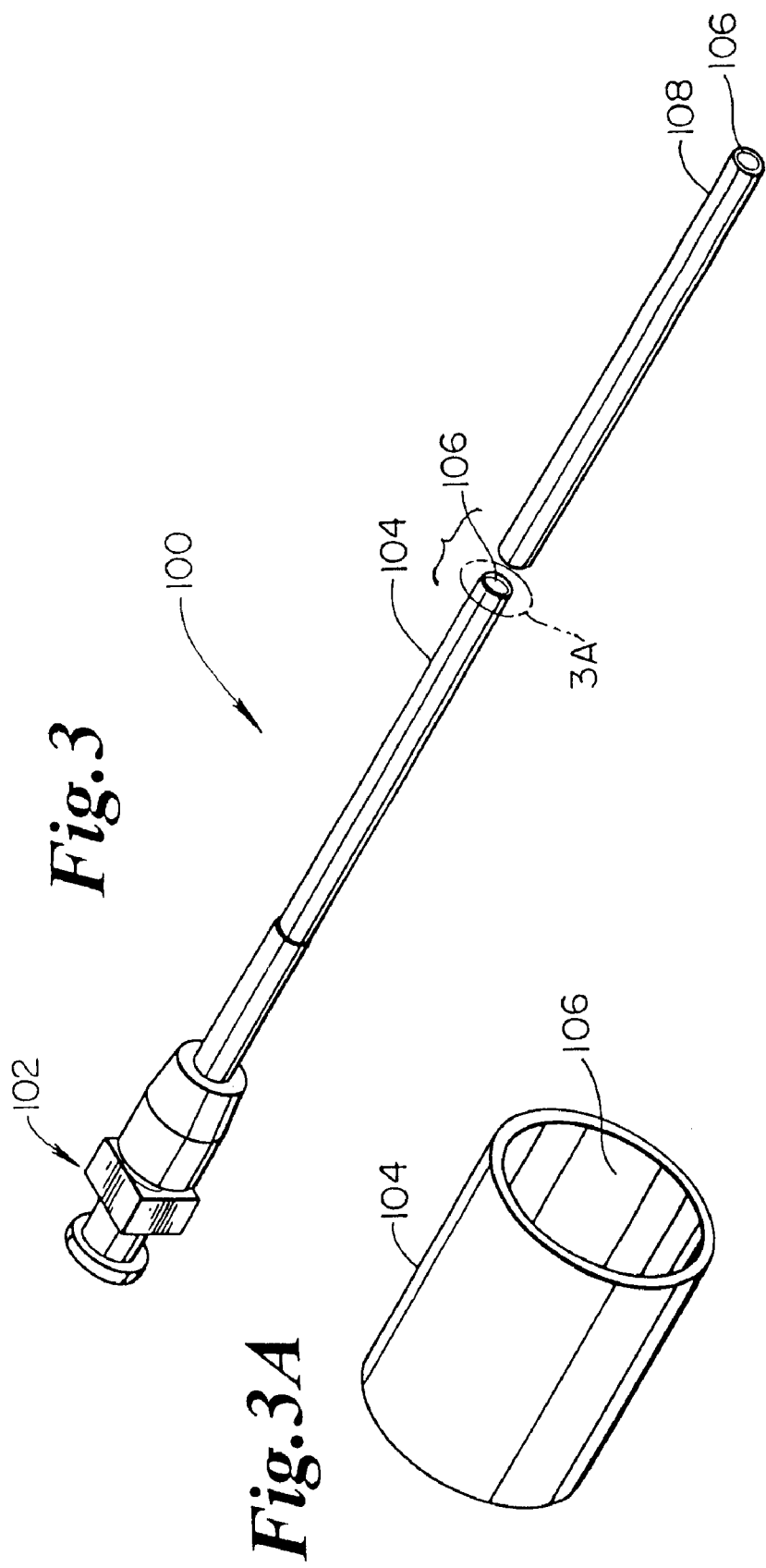

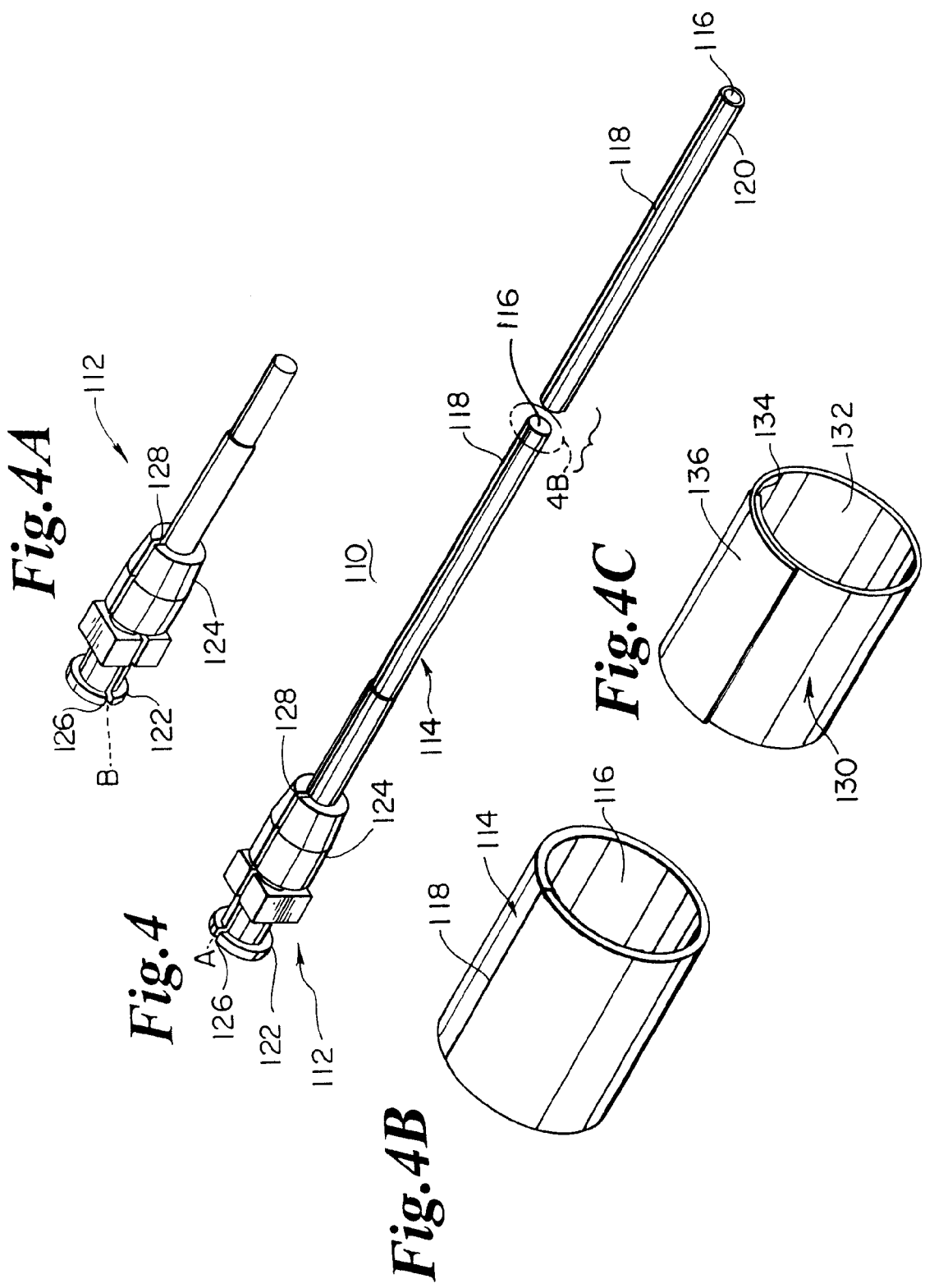

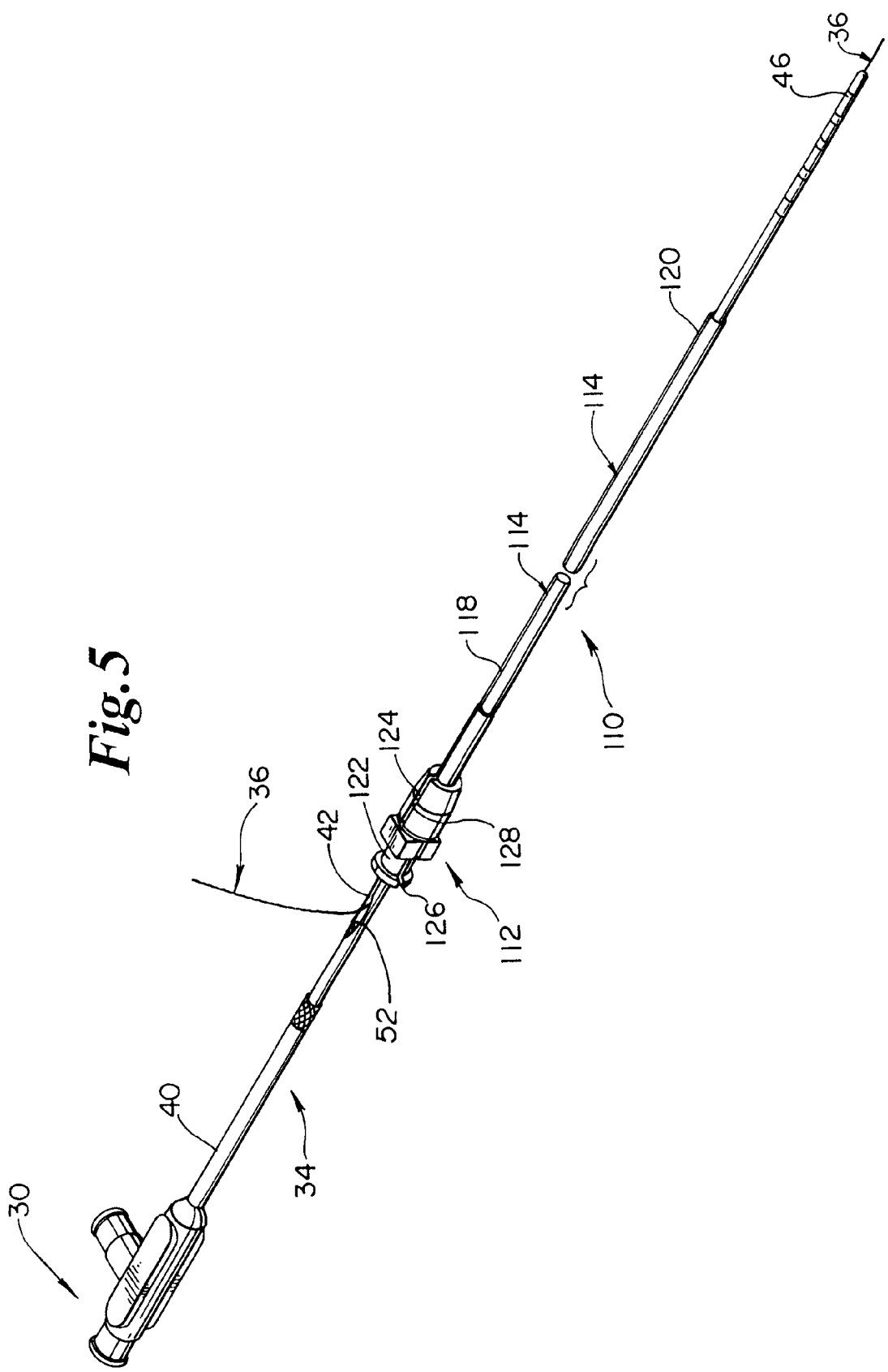

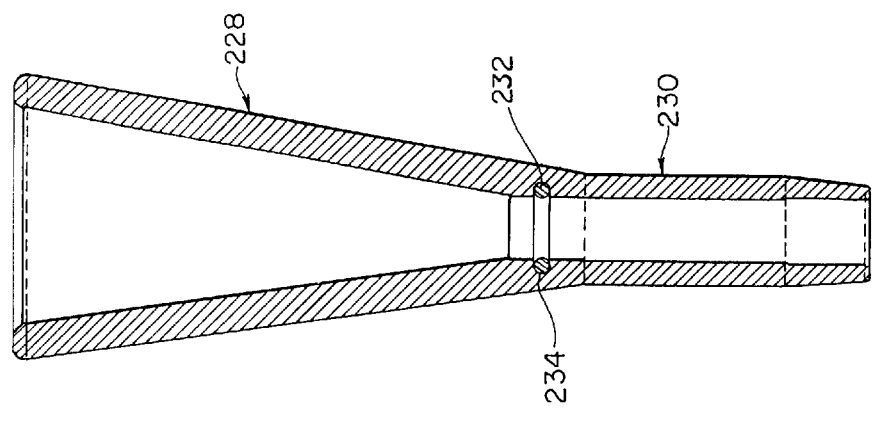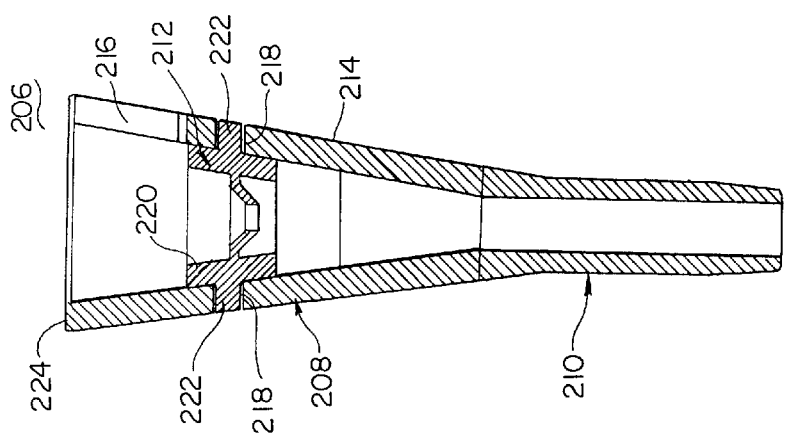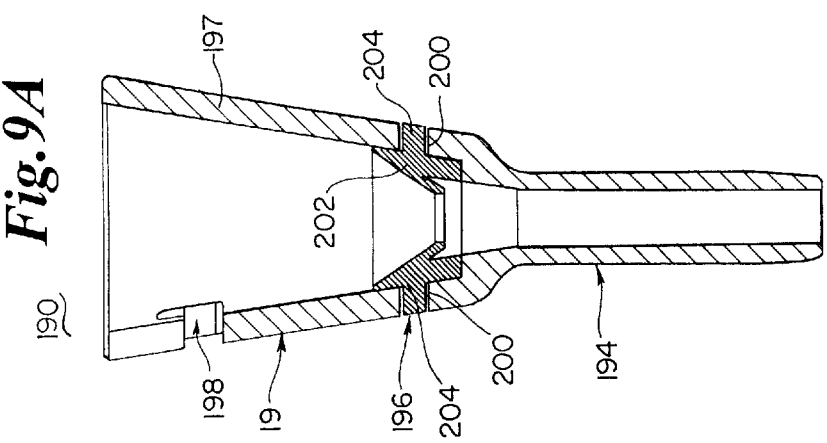

MULTI-SIZE CONVERTIBLE CATHETER

RELATED APPLICATIONS

This is a continuation-in-part application of U.S. patent application Ser. No. 08/926,200, filed on Sep. 9, 1997, now U.S. Pat. No. 6,007,522, issued Dec. 28, 1999 entitled "Single Operator Exchange Biliary Catheter", which claims priority under 35 U.S.C. §119(e) to provisional application U.S. Ser. No. 60/025,235, filed Sep. 13, 1996, entitled "Single Operator Exchange Biliary Catheter". This application is related to U.S. Pat. No. 6,346,093, issued Feb. 12, 2002, entitled "Single Operator Exchange Biliary Catheter With Common Distal Lumen," the disclosure of which is incorporated herein by reference.

FIELD OF THE INVENTION

The present invention relates to a multi-size convertible catheter capable of having its outer diameter altered by removing superimposed, peelable layers. The multi-size catheter is particularly useful in conjunction with an endoscope for accessing the alimentary canal within the human anatomy and methods of using such a catheter. The peelable layers may be selectively removed from the multi-size catheter in order to obtain an outer diameter for the catheter that is less than, but approximate to, the inner diameter of the working channel of the endoscope.

DESCRIPTION OF THE PRIOR ART

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with fluoroscopy and guidewires.

Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference.

In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate the papilla of vater leading to the common bile duct and the pancreatic duct. A catheter is guided through the lumen of the endoscope until a distal tip of the catheter emerges from the opening at the distal end of the endoscope.

The catheter may be used for accessing the biliary tree. The distal end of the catheter is guided through the orifice to the papilla of vater (located between the sphincter of oddi) leading to the common bile duct and the pancreatic duct. A guidewire may be used in conjunction with the catheter to facilitate accessing a desired location within the biliary tree. The guidewire is inserted in an opening at a proximal end of the catheter and guided through the catheter until it emerges from the distal end of the catheter.

If visualization of the common bile duct is desired, the guidewire is guided into the common bile duct. The catheter is advanced over the guidewire, as previously described, until the distal end of the catheter is positioned in the common bile duct at the desired location. The catheter is now in position for delivery of contrast media for fluoroscopic visualization of anatomical detail within the common bile duct. Once the guidewire is in place relative to the targeted area, it is highly desirable to maintain that position of the guidewire during subsequent catheter procedures, including catheter exchange procedures.

Present biliary endoscopic procedures include the use of multi-lumen catheters for endoscopic retrograde cholangiopancreatography, endoscopic retrograde sphincterotomy, the use of balloon catheters having retrieval balloons, and other therapeutic and diagnostic procedures. As described in general above, these present biliary endoscopic procedures are performed using guidewire techniques. The present devices utilized in these procedures are at least 180 cm long since they pass through the endoscope, which is commonly at least 150 cm long. Therefore, when using a standard catheter having a guidewire lumen extending the full length of the catheter, guidewires used during these procedures must be at least 400 cm in length to accommodate the exchanging of different devices while maintaining access and position within the biliary tree. The exchange of devices over a 400 cm guidewire is both time consuming and cumbersome.

Due to the length of the guidewire, physicians require at least two assistants in the room to perform the biliary endoscopic procedure. Typically, one assistant is responsible for the patient and device-related concerns, while the other assistant is responsible for the guidewire. The additional hands required due to the length of the guidewire results in a relatively more time consuming and costly procedure.

It is desirable to have an exchange catheter suitable for use within the alimentary canal for accessing targeted anatomical regions, such as the biliary tree, having features which facilitate rapid exchange and allow an exchange procedure to be performed by a single operator. It is desirable to have a biliary exchange catheter which may be used in connection with a shorter guidewire, and requires less personnel for performing biliary procedures. It is desirable to have a biliary exchange catheter which limits the amount of guidewire over which the catheter must travel.

It is also desirable to have a biliary rapid exchange catheter which may be convertible for use between conventional guidewire techniques and rapid exchange guidewire techniques. It is desirable to have a biliary rapid exchange catheter which is easily removable from the guidewire, and adaptable for use with most catheter systems used within the alimentary canal.

SUMMARY OF THE INVENTION

The present invention relates to a multi-size convertible catheter for use in biliary endoscopic procedures. In particular, the present invention overcomes many of the disadvantages of the prior art by providing a catheter that incorporates the structural features of an endoscope sheath into a single medical device. Specifically, in preferred embodiments, the multi-size catheter comprises a plurality of peelable layers forming the outer diameter of the catheter. The peelable layers may be individually removed allowing the outer diameter of the catheter to be varied.

A preferred embodiment for the multi-size convertible catheter includes a catheter shaft having a proximal end and a distal end. The multi-size catheter additionally includes a guidewire lumen carried by the shaft extending from a location proximal of the distal end of the shaft to a location proximate the distal end of the shaft. Means are provided for accessing the guidewire lumen from a location exterior to the catheter shaft, located a substantial distance distal of the proximal end of the shaft. The means for accessing the guidewire lumen may include an open channel extending through a wall of the catheter shaft. The multi-size catheter further includes at least one, but preferably a plurality of peelable layers co-axially disposed over the catheter shaft. Means are provided for removing individual peelable layers from the exterior of the multi-size catheter. The means for removing the peelable layer preferably includes a perforated line within the peelable layer. The perforated line may be slit, whereby the peelable layer may be separated from the catheter by extracting the peelable layer from the slit.

In one embodiment, the multi-size convertible catheter has an outer diameter sufficient for placement within the largest endoscope working channels. The tolerance between the outer diameter of the catheter and the working channel is smaller than the diameter of a guidewire. Guidewire movement, therefore, is constrained to within the guidewire channel of the catheter only. The guidewire is effectively stopped from slipping out of guidewire channel thereby eliminating the potential for the guidewire to become pinched and restrict desired movements of both the guidewire and the catheter.

In another embodiment, the multi-size convertible catheter is adapted for endoscopes of varying working channel diameters. The multi-size catheter comprises an outer diameter defined by a plurality of superimposed co-axially disposed peelable layers. Before positioning the multi-size catheter within the working channel of an endoscope, the peelable layers may be selectively removed in order to obtain an outer diameter for the catheter that is less than, but approximate to, the inner diameter of the working channel of the endoscope. A correct fit between the catheter and the working channel of an endoscope reduces the potential for the guidewire to slip out of the guidewire channel and become pinched.

BRIEF DESCRIPTION OF THE DRAWINGS

The invention will be further described with reference to the accompanying drawings, wherein like numbers refer to like parts in several views and wherein:

FIG. 1 is a perspective view of a catheter in accordance with the present invention having a U-shaped channel and guidewire lumen for directing a guidewire along its shaft and for facilitating rapid catheter exchange;

FIG. 1C is an enlarged fragmentary perspective view of the encircled catheter section of FIG. 1 at 1C;

FIG. 3 is a perspective view of an endoscope exchange sheath assembly, without slit, suitable for receiving the catheter of FIG. 1;

FIG. 3A is an enlarged fragmentary perspective view of the encircled sheath section of FIG. 3 at 3A;

FIG. 4 is a perspective view of an alternative embodiment sheath assembly having a slit sheath and two-piece hub, shown in unlocked position;

FIG. 4A is a perspective view of the two-piece hub of FIG. 4 in locked position;

FIG. 4B is an enlarged fragmentary perspective view of the encircled sheath section of FIG. 4 at 4B, having a slit;

FIG. 4C is an enlarged fragmentary perspective view of a sheath section, having an overlap, an alternate embodiment of the sheath in FIG. 4B;

FIG. 5 is a perspective view of the catheter of FIG. 1 inserted through the endoscope sheath assembly of FIG. 4;

FIG. 7A is a perspective view of the sheath assembly of FIG. 7, having the catheter removed;

FIG. 9A is an enlarged, cross-sectional view of an alternative embodiment of the introducer of FIG. 8;

FIG. 9B is an enlarged, cross-sectional view of another alternative embodiment of the introducer of FIG. 8;

FIG. 9C is an enlarged, cross-sectional view of another alternative embodiment of the introducer of FIG. 8;

DETAILED DESCRIPTION OF THE INVENTION

Figure 1B:
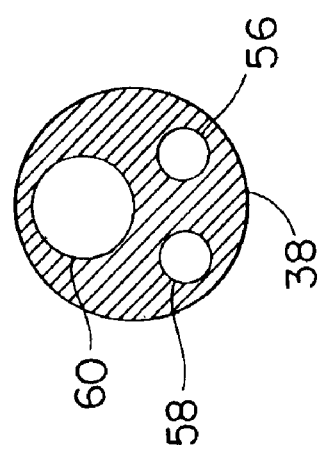
FIG. 1B is a cross-sectional view of the catheter with guidewire of FIG. 1 taken along the line 1B—1B.

FIG. 1 shows a perspective view of a catheter assembly 30 in accordance with the present invention. Catheter assembly 30 is used in catheter procedures for accessing targeted anatomical regions through the alimentary canal. The present invention incorporates features which allow rapid exchange of the catheter by a single operator. The catheter of the present invention allows shorter length guidewires to be used, resulting in procedures which require less medical personnel, are less time consuming, and less costly. Additionally, the present invention is adaptable to most catheter devices used for catheter procedures within the alimentary canal.

Catheter assembly 30 includes a catheter hub assembly 32 and a catheter 34, having a guidewire 36 passing through a portion thereof. Catheter 34 includes a shaft 38, which in general terms has a proximal end 40, a U-channel 42, a distal tip region 44, a distal end 46 and various lumens described in greater detail below. Catheter hub assembly 32 is operably connected to proximal end 40 of shaft 38. Catheter hub assembly 32 is preferably configured to couple to ancillary devices allowing access to a lumen within shaft 38.

Shaft 38 is a generally tubular shaped member having a generally uniform outer shape at proximal end 40. Shaft 38 may be sized for slidable passage through the lumen of an endoscope (not shown). Shaft 38 is preferably formed in an extrusion process. Shaft 38 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphincterotomes, cytology devices, and devices for stone retrieval and stent placement.

In a preferred embodiment, shaft 38 further includes a distal taper 48 which tapers to distal tip region 44. Additionally, tip region 44 may include high contrast, color coded distal markers 50. Finally, distal end 46 may be radiopaque for fluoroscopic visualization of distal tip region 44 during a catheter procedure. It should be understood, however, that these additional features are in no way required elements.

U-channel 42 of shaft 38 extends between a first, proximal channel end 52 and a second, distal channel end 54. U-channel 42 serves to contain, but not necessarily constrain, guidewire 36, between channel proximal end 52 and channel distal end 54. The term "U-channel" refers to a channel shape that allows radial removal of guidewire 36 from the channel 42, and need not be strictly in the shape of the letter U. Channel 42 in the preferred embodiment is sufficiently large to allow unhindered radial guidewire 36 movement out of channel 42. Further, the channel walls and radial opening are substantially equal to or slightly larger than the diameter of a guidewire lumen, described in greater detail below. Although it is recognized that proximal channel end 52 may be located at any location distal of proximal end 40 of shaft 38, channel distal end 54 is preferably located between 10 and 40 cm from distal end 46 of catheter shaft 38.

Figure 1A:
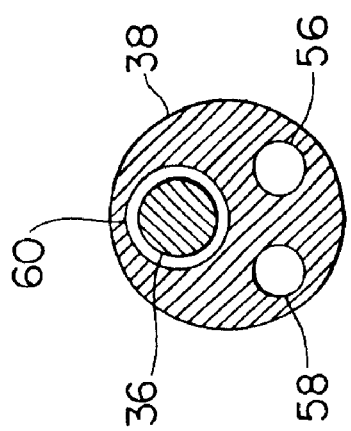
FIG. 1A is a cross-sectional view of the catheter of FIG. 1 taken along the line 1A—1A.

Finally, as shown in FIG. 1A, which is a cross-sectional view of shaft 38 taken along line 1A—1A at a location proximal of channel proximal end 52, shaft 38 includes ancillary lumen 56, ancillary lumen 58 and guidewire lumen 60.

Ancillary lumen 56 and ancillary lumen 58 extend longitudinally between proximal end 40 and distal end 46 of shaft 38. Ancillary lumen 56 and ancillary lumen 58 may be injection lumens, allowing for high contrast media flow capability for bubble-free opacification and for excellent visualization of a desired anatomical region. Additionally or alternatively, ancillary lumen 56 and/or ancillary lumen 58 may be used for or as part of other ancillary devices, such as a cutting wire lumen or a retrieval balloon lumen.

Guidewire lumen 60 extends longitudinally between proximal end 40 and distal end 46 of shaft 38 in the preferred embodiment. Further, guidewire lumen 60 is sized to receive guidewire 36. Guidewire lumen 60 may be a tubular member which is extruded integral catheter shaft 38, or alternatively, guidewire lumen 60 may be a separate tubular member which is coupled to catheter shaft 38. Although in one preferred embodiment the guidewire lumen 60 is a tubular member which is located proximate distal end 46 of catheter shaft 38, it is recognized that guidewire lumen 60 may be formed anywhere along shaft 38, may be an extension of shaft 38 coupled to distal end 46, or guidewire lumen 60 may run the entire length of shaft 38.

Referring to FIG. 1B, a cross-sectional view of shaft 38 taken along line 1B—1B of FIG. 1 is shown. Guidewire 36 may access guidewire lumen 60 at a point proximal channel distal end 54. Guidewire 36 extends within channel 42 to channel distal end 54, continuing within guidewire lumen 60 through distal tip region 44, and exiting through cm opening in distal end 46.

Referring to FIG. 1C, a section of catheter shaft 38 having U-channel 42 is shown. The embodiment shown also includes ancillary lumens 56 and 58. Sections of shaft 38 proximate the channel proximal end 52 and distal channel distal end 54 contain guidewire lumen 60 in communication with U-channel 42. In one embodiment, U-channel 42 has an interior, closed-side geometry, substantially the same as the geometry of guidewire lumen 60. Further, U-channel 42 walls are spaced further than a diameter of guidewire 36 such that guidewire 36 moves freely into and out of U-channel 42.

Catheter shaft 38 can be configured such that U-channel 42 is defined separately from guidewire lumen 60. With this approach, guidewire lumen 60 is divided into two sections; a first section extending between proximal end 40 of shaft 38 and channel proximal end 52; and a second portion extending between channel distal end 54 and distal end 46 of shaft 38. Alternatively, the shaft can be configured to define guidewire lumen 60 as extending longitudinally between proximal end 40 and distal end 46 of shaft 38. In the alternative embodiment, between channel proximal end 52 and channel distal end 54, guidewire lumen 60 is integral with U-channel 42. In other words, guidewire lumen 60 defines a portion of U-channel 42 such that spacing between outer walls of U-channel 42 is equal to a diameter of guidewire lumen 60. Regardless of how guidewire lumen 60 and U-channel 42 are defined, U-channel 42 provides for access to guidewire lumen 60 at channel distal end 54. In this regard, channel distal end 54 can be enlarged to more easily direct guidewire 36 into guidewire lumen 60.

Guidewire lumen 60 and U-channel 42 allow rapid exchange of catheter assembly 30 when an alternative catheter is necessary during a certain medical-procedure. Shorter length guidewires may be used since guidewire 36 does not pass through shaft proximal end 40 and hub assembly 32, but rather exits the catheter shaft 38 at U-channel 42 located substantially distal from proximal end 40. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) guidewire within the targeted anatomical region is eliminated, reducing the overall costs of the procedure.

Figure 2A:
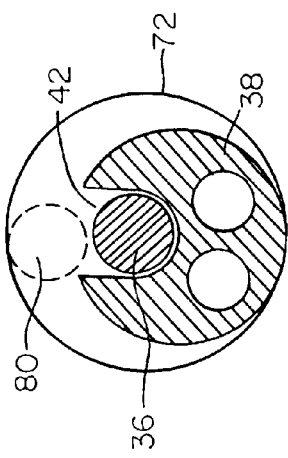
FIGS. 2A–2D are cross-sectional views of the catheter of FIG. 1 located within increasingly larger endoscope channels.

Referring to FIGS. 2A through 2D, cross-sectional views of endoscope working channels 70–76 containing a catheter according to FIG. 1 are shown. In the examples illustrated in FIGS. 2A through 2D, working channel inside diameters 70, 72, 74, and 76 are 2.8, 3.2, 3.8, and 4.2 mm, respectively. FIG. 2A illustrates catheter shaft 38 having ancillary lumens 54 and 56, U-channel 42, and guidewire 36 within U-channel 42. Further, shaft 38 is shown within a first size endoscope working channel 70. In FIG. 2A, guidewire 36 is effectively radially constrained by small sized working channel 70 that closely surrounds U-channel 42.

Figure 2B:
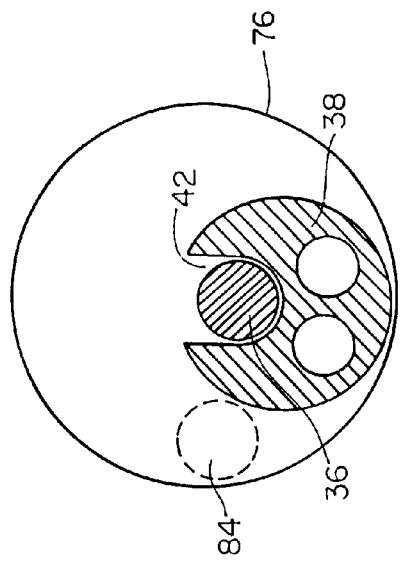
Figure 2C:
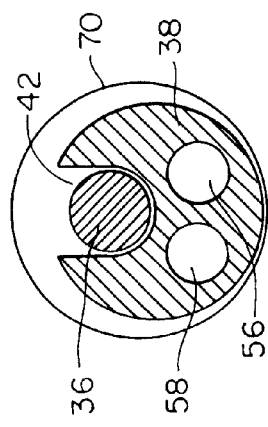

FIG. 2B illustrates catheter containment within a second sized working channel 72, slightly larger than the working channel 70 of FIG. 2A. In FIG. 2B, guidewire 36 is able to move out of U-channel 42 to a position denoted with dashed lines at 80. FIG. 2C shows shaft 38 contained within a third, even larger sized working channel 74. Guidewire 36 is able to move completely out of U-channel 42 to position 82 shown with dashed lines. Finally, FIG. 2D demonstrates catheter shaft 38 within a fourth size working channel 76. In this even larger working channel, guidewire 36 lies within an even larger cross-sectional area, and is able to move to a position shown in FIG. 2D with dashed lines at 84.

As shown with the larger endoscope working channels (FIGS. 2C and 2D), the potential for guidewire 36 to slip out of U-channel 42 creates a potential for the guidewire 36 to become pinched and restrict desired movements of both guidewire 36 and catheter shaft 38. For this reason, when larger endoscope working channels are used, an exchange sheath having a sufficiently small inner diameter so as to constrain guidewire movement to within the catheter U-channel 42 is employed with the preferred embodiment. Generally speaking, an endoscope exchange sheath in accordance with the preferred embodiment allows for use of a radially accessible guidewire, which is longitudinally aligned with the catheter, while presenting a circular profile to an endoscope and mitigating guidewire pinching problems between the catheter and the endoscope working channel wall.

Referring to FIG. 3, an endoscope exchange sheath assembly 100 having sheath hub assembly 102 and a sheath 104 is shown. The sheath 104 includes a lumen 106 and a distal end 108. FIG. 3A shows a section of sheath 104, having lumen 106 for receiving a catheter. Basically, with reference to FIG. 1, catheter 34 is fed through lumen 106 of sheath 104 such that sheath 104 encompasses guidewire 36 within U-channel 42. Sheath 104 is adapted to be disposed within an endoscope working channel, thereby providing a smaller diameter channel than that of the surrounding endoscope working channel constraining the guidewire 34 (FIG. 1) to the U-channel 50 (FIG. 1), and mitigating the potential problems shown in FIGS. 2C and 2D.

Referring to FIG. 4, an alternate endoscope exchange sheath assembly 110 is shown. Sheath assembly 110 includes a two-piece hub assembly 112 and a sheath 114 defining lumen 116 and having slit 118 extending longitudinally over its length, terminating at distal end 120. Slit 118 in sheath 114 is shown in more detail in FIG. 4B.

Referring again to FIG. 4, two-piece hub assembly 112 has a proximal hub portion 122 and a distal hub portion 124, having a proximal slit 126 and a distal slit 128, respectively. Sheath slit 118 is in communication with hub slits 126 and 128, allowing a guidewire (not shown) to be radially slid into or out of sheath assembly 110. Proximal hub portion 122 is shown unlocked (position "A") in FIG. 4, aligning hub proximal slit 126 with hub distal slit 128 and sheath slit 118, providing a continuous slit for guidewire radial movement into and out of the sheath assembly 110. Proximal hub portion 122 is shown locked, in position "B", in FIG. 4A, whereby proximal hub slit 126 is rotated with respect to distal hub slit 128, preventing a guidewire (not shown) within hub assembly 112 from being moved radially out of hub assembly 112. Proximal hub portion 122 is set to position B (FIG. 4A) when radial guidewire movement is not desired.

FIG. 4C illustrates a portion of an alternate embodiment sheath 130 having a lumen 132, a sheath wall opening 134 and sheath wall overlap 136. A guidewire (not shown) is able to be slid out of lumen 132 of sheath 130 by maneuvering the guidewire into sheath wall opening 134 and through overlap 136.

Referring to FIG. 5, catheter assembly 30 depicted in FIG. 1 is shown inserted within endoscope exchange sheath assembly 110 depicted in FIG. 4. More particularly, catheter 34 is inserted through slitted sheath assembly 110, extending distally out sheath distal end 120. Guidewire 36 (shown partially in FIG. 5) is positioned within U-channel 42 of catheter 34, along guidewire lumen 60 (FIG. 1B), and extends from shaft distal end 46. Further, guidewire 36 is engaged by hub assembly 112. More particularly, guidewire 36 passes within and is engaged by proximal slit 126 and distal slit 128 of hub assembly 112. Sheath proximal hub portion 122, having proximal slit 126, is shown in locked position relative to sheath distal hub portion 124, having distal slit 128. Thus, in the locked position, hub assembly 112 of sheath assembly 110 prevents radial withdrawal of guidewire 36, otherwise inserted in U-channel 42 of catheter 34, from distal the channel proximal end 52.

Figure 2D:
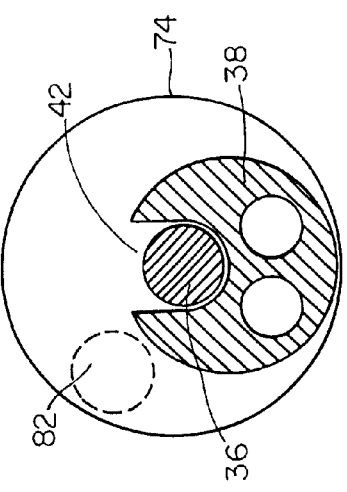
Figure 6:
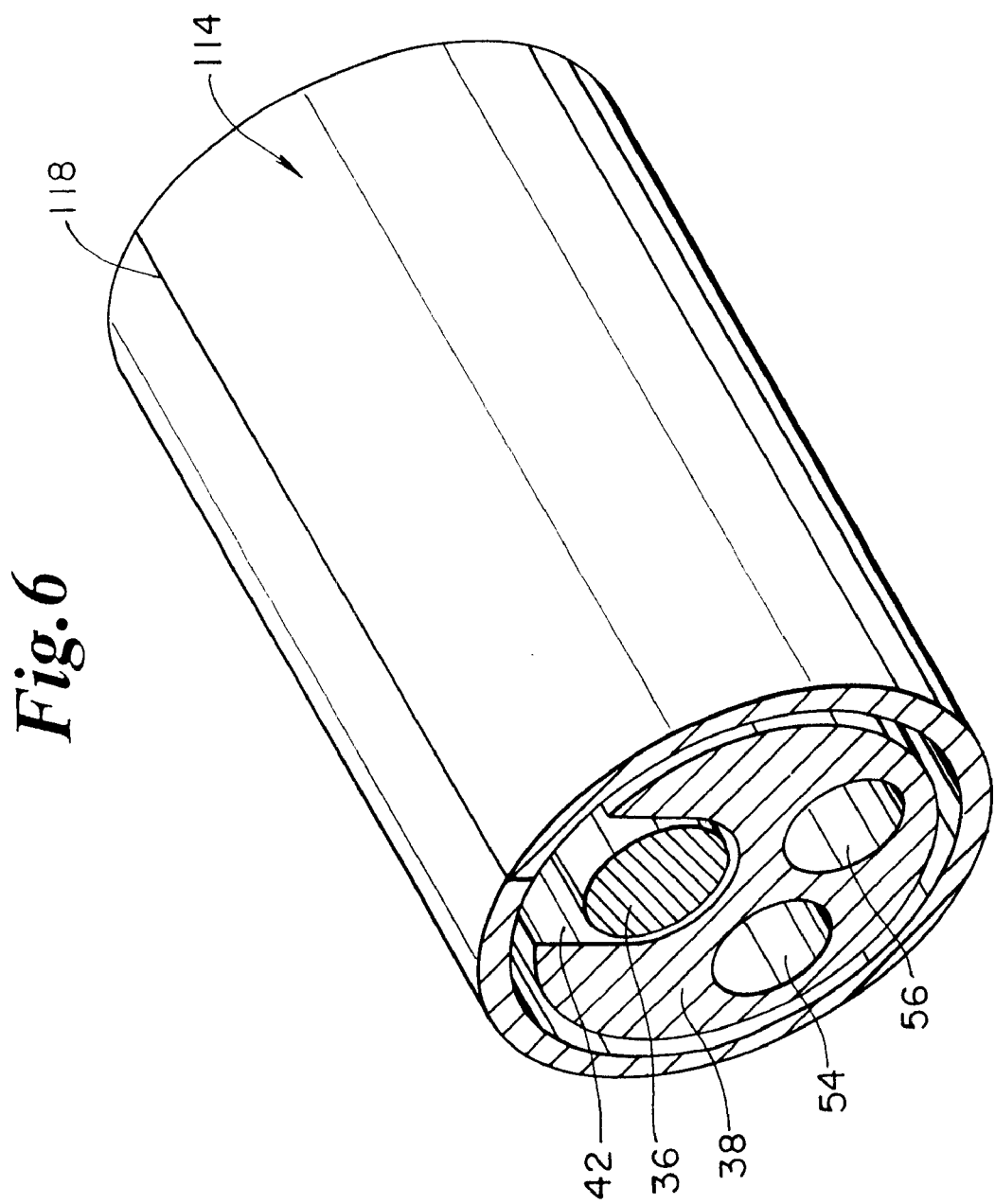
FIG. 6 is a perspective view of an endoscope sheath section containing a catheter having a U-shaped channel containing a guidewire.

Referring to FIG. 6, a section of FIG. 5 is shown in detail, having endoscope sheath 114 containing catheter shaft 38, which further maintains guidewire 36 within U-channel 42. As shown, sheath 114 is able to constrain movement of guidewire 36 from U-channel 42 when sheath 114 is within a larger endoscope working channel, for example as illustrated in FIGS. 2C and 2D. Importantly, the sheath 114 embodiment illustrated in FIG. 6 includes longitudinal slit 118, allowing guidewire 36 to be peeled from catheter shaft 38 and endoscope sheath 114. In other words, as previously described, U-channel 42 is sized larger than guidewire 36 such that guidewire 36 can displace radially from U-channel 42. Sheath 114 prevents undesired displacement of guidewire 36 from U-channel 42 under normal operating conditions. However, if adequate radial force is placed on guidewire 36 by an operator, guidewire 36 will separate sheath 114 along slit 118 such that guidewire 36 is displaced from sheath 114 and U-channel 42.

Figure 7:
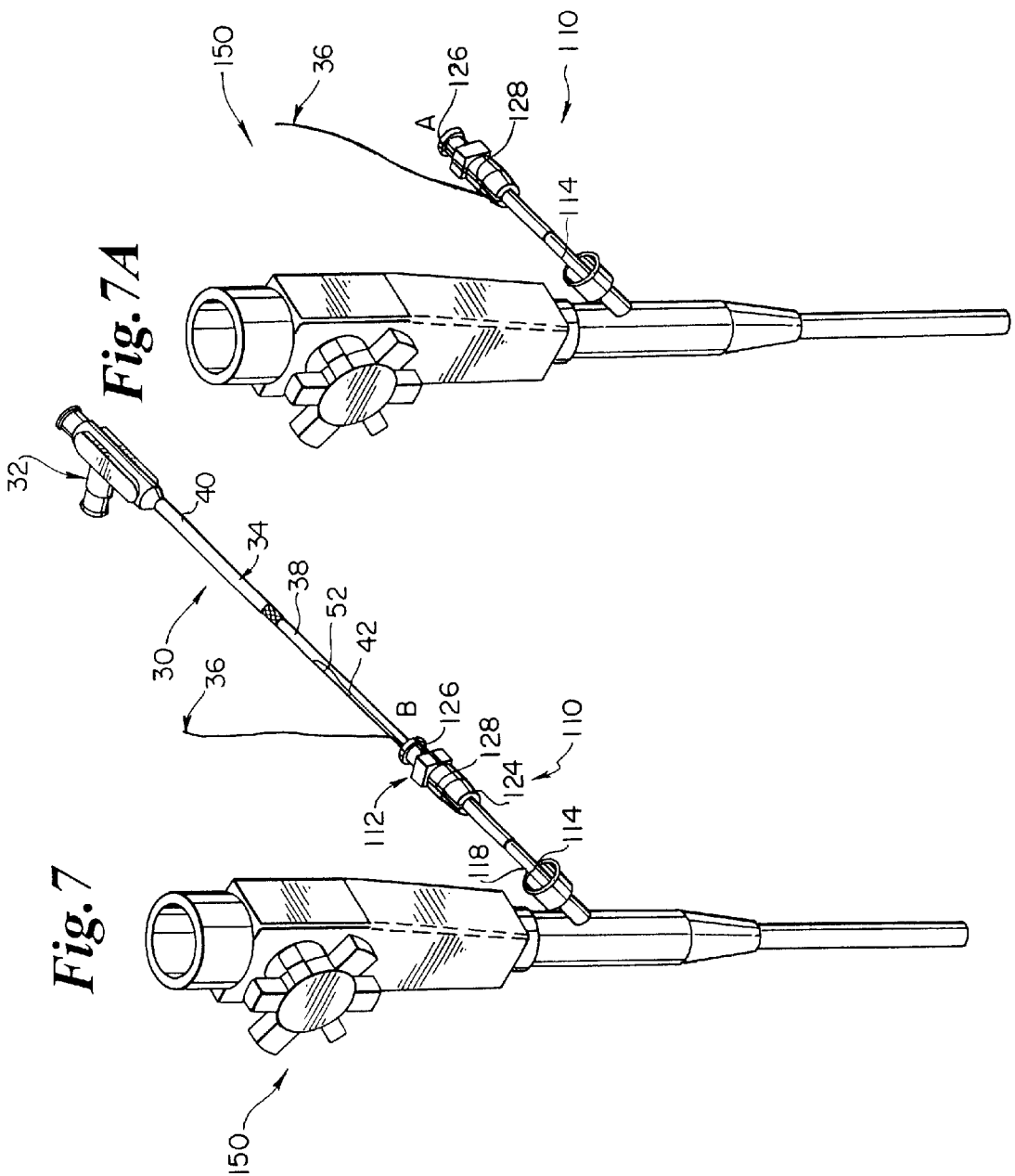
FIG. 7 is a partial perspective view of a guidewire within the catheter of FIG. 1 inserted through the endoscope sheath assembly of FIG. 4, which is in turn within an endoscope.

Referring to FIG. 7, guidewire 36 is shown inserted within catheter assembly 30 of FIG. 1, which is inserted through endoscope sheath assembly 110 of FIG. 4, which is in turn within an endoscope 150. Sheath assembly 110 includes sheath 114 that has slit 118 and two-piece hub assembly 112, shown at a locked position "B" (also in FIG. 4A). Having hub assembly 112 locked prevents guidewire 36 from moving radially out of sheath 114 through slit 118. Guidewire 36 can be restrained from longitudinal movement by applying finger pressure on the guidewire 36 against hub assembly 112.

Referring to FIG. 7A, endoscope 150 and sheath assembly 110 of FIG. 7 are shown without the catheter assembly 30 inserted, as after catheter withdrawal. Sheath hub assembly 112 is shown in unlocked position at "A" (also in FIG. 4). Having hub assembly 112 unlocked allows radial movement of guidewire 36 out of sheath 114 through slit 118, but such movement may be restrained by trapping guidewire 36 against the outside of sheath 114 using one finger, providing ease of guidewire 36 control during catheter exchanges.

In one possible endoscopic procedure, an endoscope 150, as illustrated in FIG. 7, is first introduced into the mouth of a patient and is guided through the patient's alimentary canal. Specifically, endoscope 150 is guided down the esophagus, through the stomach, past the pyloric sphincter of the stomach and into the duodenum. Endoscope 150 has a lumen extending longitudinally between its proximal end and the distal end.

Endoscope 150 is guided through the alimentary canal until a distal end (not shown) of endoscope 150 is proximate the target area within the anatomy to receive treatment. In an endoscopic biliary procedure, endoscope 150 is guided into the duodenum until the opening at the distal end of the endoscope 150 is proximate the papilla of vater. The papilla of vater is located between the sphincter of oddi, which leads to the common bile duct, hepatic, and pancreatic ducts. The proximal end (shown in FIGS. 7 and 7A) of endoscope 150 extends and remains outside the mouth of the patient.

With endoscope 150 properly positioned within the patient, catheter assembly 30 is prepared for insertion into the endoscope. First, guidewire 36 is fed into the guidewire lumen 60 (FIGS. 1A–1C) of shaft 38. More particularly, a distal end of guidewire 36 is placed within U-channel 42, distal the channel proximal end 52. The guidewire 36 is then fed to channel distal end 54 (FIG. 1) into guidewire lumen 60. Finally, guidewire 36 is fed through shaft 38 to distal tip region 40 (FIG. 1). In one method, catheter 32 is then inserted directly into endoscope 150 working channel. This method may be practiced with an endoscope having a sufficiently small working channel inside diameter, as illustrated in FIG. 2A, to constrain guidewire 36 movement without a sheath.

However, in a preferred method (with reference to FIG. 7), catheter assembly 30, threaded with guidewire 36, is inserted into sheath assembly 110, thereby constraining guidewire 36 from slipping radially out of U-channel 42. More particularly, catheter 34 is inserted into endoscope 150 working channel, but leaving channel proximal end 52 proximate sheath hub assembly 112, and leaving a portion of guidewire 36 extending from the channel proximal end 52 as well. Notably, sheath hub assembly 112 includes hub slits 126 and 128 which receive a portion of guidewire 36. Thus, in the preferred embodiment, hub assembly 112 is locked, preventing unwanted radial guidewire 36 movement. In a preferred method, the loading of guidewire 34 into catheter shaft 38 arid catheter shaft 38 into sheath assembly 110 is done prior to inserting endoscope 150 into a patient (not shown).

Endoscope sheath 114, containing catheter shaft 38, is inserted into endoscope 150 working channel. Endoscope sheath 114 serves to constrain radial guidewire 36 movement over the approximate length of U-channel 42. Catheter shaft 38 and sheath 114 are inserted together into endoscope 150 until both are near a distal end (not shown) of endoscope 150. Catheter shaft 38 and sheath 114 may be, either or both, advanced until exiting the distal end of endoscope 150.

In one method, guidewire 36 is advanced until guidewire 36 distal tip is positioned within the target area in the biliary tree (including the common bile, hepatic or pancreatic ducts). For example, the distal tip of guidewire 36 may be guided through the orifice leading to the papilla of vater for access to the biliary tree. Catheter shaft 38 may then be advanced over guidewire 36, tracking catheter assembly 30, until catheter distal tip region 40 (FIG. 1) exits distal end of endoscope 150 and is positioned within the desired duct. In another method, guidewire 36 and catheter assembly 30 are advanced together until catheter distal end 42 (FIG. 1) is positioned at the target area. It is also recognized that the catheter could be first advanced to near the target area, followed by inserting the guidewire when needed to advance the catheter further.

Once guidewire 36 is in position at the target area, catheter procedures, including injecting contrast media, such as radiopaque dye, through ancillary lumens 56 or 58 (FIG. 1A–1C) into the common bile duct for visualization of the duct, can be performed. After the desired catheter procedure has been completed, catheter assembly 30 can be exchanged or removed from endoscope 150, leaving guidewire 36 in position for other catheter procedures. Catheter assembly 30 and sheath assembly 110 may also be removed together.

One method of withdrawing catheter 34 from endoscope 150 is possible using either a slitted/overlapped endoscope sheath 114 as depicted in FIGS. 4 through 5C, or a sheath 104 without a slit as depicted in FIGS. 3 through 3A. Using this method, best visualized with reference to FIG. 7, guidewire 36 is held to prevent longitudinal movement while catheter 34 is retracted within endoscope sheath 114 (or 104). Catheter 34 retraction leaving the guidewire 36 in position within the patient is enabled by U-channel 42 being radially open to guidewire 36 removal in catheter shaft 36. Once catheter retraction has brought channel distal end 54 (FIG. 1) to a point proximate sheath hub assembly 112, only a relatively short portion of guidewire 36, from channel distal end 54 to distal end 46 (FIG. 1) of catheter shaft 38, remains within catheter 34. A single operator can remove this remaining portion of guidewire 36 from catheter 34 by first slightly retracting catheter assembly 30 (while still holding guidewire 34 in place) out of sheath assembly 110 (or 100), such that a portion of guidewire 36 is accessible distal of catheter distal end 46. In other words, a small portion of guidewire 36 is accessible between distal end 46 of catheter 34 and distal hub portion 124 of sheath assembly 110. The accessible portion of guidewire 36 is then held by the operator, while withdrawing the remaining portion of catheter 34 completely over guidewire 36. In an alternative method, the distal end of the endoscope can include an elevator which could be utilized to lock the distal end of the guidewire in position while the catheter is removed.

Exchange of endoscope sheath assembly 110 may be desired, as when a stent (not shown) is to be advanced over guidewire 36, and the stent has a larger outside diameter than can be accommodated by the sheath 114. One method of exchanging an endoscope sheath assembly 110 may be used where sheath 114 is slitted as in FIG. 4B, or overlapped, as in sheath 130 in FIG. 4C. Referring to FIG. 7A, two-piece hub assembly 112 is turned to the unlocked position "A" (also shown in FIG. 4). Guidewire 36 is pulled radially away from sheath hub assembly 112 and through slit 118 in sheath 114. Guidewire 36 is then held, preferably against some portion of endoscope 150, to prevent guidewire 36 from being dislodged from position within the patient. Sheath 114 is retracted from endoscope 150, guidewire 36 being "peeled" away from sheath 114. Sheath retraction is continued until sheath 114 is completely outside of endoscope 150 and over guidewire 36. At this point, guidewire 36 is within endoscope 150 working channel, and stents, catheters, and endoscope sheaths may be advanced over guidewire 36.

Another method of exchanging both endoscope sheath assembly 110 and catheter assembly 30 may be used where the sheath 114 is slitted as in FIG. 4B, or overlapped, as in sheath 130 in FIG. 4C. Referring to FIGS. 7 and 7A, two-piece hub assembly 112 is turned to the unlocked position "A" (FIG. 7A). Guidewire 36 is pulled radially away from U-channel 42 of catheter 34, from hub assembly 112 and through slit 118 in sheath 114. Guidewire 36 is then held, preferably against some portion of endoscope 150, to prevent guidewire 36 from being dislodged from position within the patient. Sheath 114 and catheter 34 are retracted from endoscope 150, with guidewire 36 being "peeled" away from sheath 114. Sheath assembly 110 and catheter assembly 30 retraction are continued until sheath 114 and catheter 34 are completely outside of endoscope 150 and over guidewire 36. At this point, guidewire 36 remains in a position within endoscope 150 and patient. A single operator can access a small portion of guidewire 36 between distal end 46 (FIG. 1) of catheter 34 to hold guidewire 36 in place while catheter assembly 30 is completely removed or disengaged from guidewire 36.

While sheath assembly 110 has been described as including a two-piece hub assembly 112 in conjunction with sheath 114, other assemblies may be used. For example, referring to FIG. 8, an alternate sheath assembly 160 is shown. Sheath assembly 160 includes an introducer 162, an attachment means 164 and a sheath 166. Similar to previous embodiments, sheath 166 defines a lumen (not shown) and includes a slit 168 extending longitudinally over its length, terminating at a distal end 170. Sheath 166 is generally identical to sheath 104 and sheath 114 previously described. Introducer 162 is attached to sheath 166 by attachment means 164 such that lumen (not shown) of sheath 166 is in fluid communication with an interior portion of introducer 162. In one preferred embodiment, attachment means 164 is a flexible membrane which seals sheath 166 to introducer 162. Alternatively, other forms of attachment, such as an adhesive or frictional engagement between introducer 162 and sheath 166 may also be useful.

Figure 8:
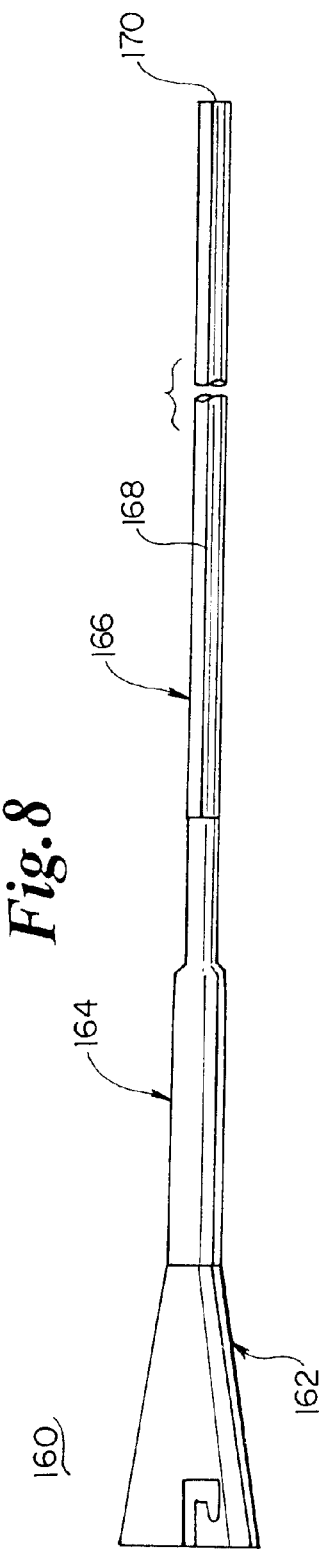
FIG. 8 is a partial perspective view of an alternative embodiment of a sheath assembly, including an introducer.
Figure 8A:
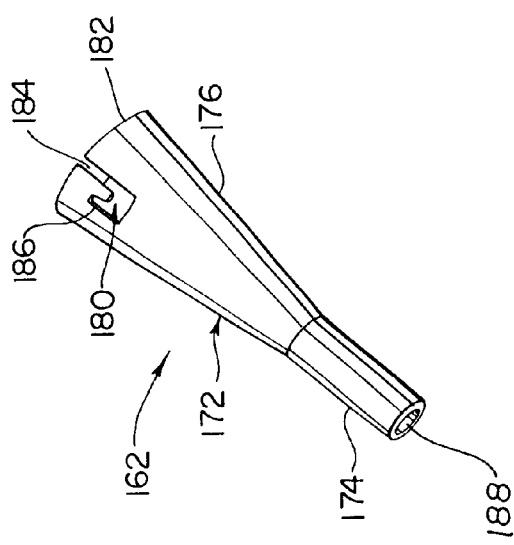
FIG. 8A is an enlarged perspective view of the introducer of FIG. 8.

Referring to FIG. 8A, introducer 162 is shown in greater detail. Introducer 162 is a funnel-shaped device including a horn 172 and a neck 174. In one preferred embodiment, horn 172 and neck 174 are integrally formed as a singular body.

Horn 172 is preferably a conically shaped body having an outer wall 176. Outer wall 176 defines an interior space and includes a guidewire-receiving notch 180 formed near proximal end 182 of horn 172. Guidewire-receiving notch 180 is preferably J-shaped and includes an entry end 184 and a locking end 186. As shown in FIG. 8A, entry end 184 is open at proximal end 182 of horn 172. Conversely, locking end 186 is closed.

Neck 174 is preferably tubular in shape, and includes a passage 188. Passage 188 is configured to be in fluid communication with interior space of horn 172. In the preferred embodiment, horn 172 and neck 174 are formed of a plastic material. Alternatively, any other semi-rigid or rigid, surgically-safe material may be used.

Referring to FIGS. 1, 8 and 8A, during use, catheter assembly 34 (FIG. 1) is inserted within sheath assembly 160. More particularly, distal end 46 (FIG. 1) of catheter shaft 38 (FIG. 1), including guidewire 36 (FIG. 1) is placed within horn 172 of introducer 162. The conical shape of horn 172 assists in directing distal end 46 of catheter shaft 38, including guidewire 36, into passage 188 of neck 174. Catheter shaft 38 continues forward within lumen (not shown) of sheath 166 until distal end 46 of catheter shaft 38 extends from distal end 170 of sheath 166.

Once properly inserted within sheath assembly 160, a proximal end of guidewire 36 (FIG. 1) is maintained within guidewire-receiving notch 180. More particularly, a portion of guidewire 36 is forced by an operator through entry end 184 of guidewire-receiving notch 180 and forced within locking end 186 thereof. In this regard, locking end 186 preferably has a diameter slightly smaller than that of guidewire 36. Thus, locking end 186 frictionally maintains guidewire 36. Conversely, guidewire 36 can easily be released from guidewire-receiving notch 180 by sliding guidewire 36 from locking end 186 and out-of entry end 184. Thus, sheath assembly 160 functions in a manner highly similar to sheath assembly 100 and sheath assembly 110 previously described.

Referring to FIG. 9A, an alternative embodiment of an introducer 190 is shown. Introducer 190 includes a horn 192, a neck 194 and a valve 196. Similar to previous embodiment, horn 192 and neck 194 are preferably integrally formed as a singular body. Horn 192 includes an outer wall 197 which defines a guidewire-receiving notch 198 and valve-receiving slots 200. Valve 196 includes a valve body 202 sized to fit within outer wall 197 of horn 192. Further, valve 196 includes ribs 204 extending from valve body 202. Ribs 204 are preferably sized to mate within valve-receiving slots 200 of horn 192. Thus, valve 196 is maintained within horn 192 via interaction of ribs 204 with valve-receiving slots 200. In this regard, valve-receiving slots 200 are preferably positioned along horn 192 proximal neck 194. Valve 196 is preferably made of a rubber-type material.

During use, introducer 190 functions in a manner highly similar to introducer 162 (FIGS. 8 and 8A) previously described. Additionally, however, valve 196 forms a seal about catheter shaft 38 (FIG. 1). Thus, upon insertion into a human body, valve 196 prevents bodily fluids, such as bile, from backing up through the sheath assembly. Additionally, valve 196 can provide for aspiration, if desired.

Referring to FIG. 9B, an alternative embodiment of an introducer 206 is shown. Introducer 206 is highly similar to introducer 190 (FIG. 9A) previously described. In this regard, introducer 206 includes a horn 208, a neck 210 and a valve 212. Horn 208 is preferably integrally formed with neck 210 and includes an outer wall 214 defining a guidewire-receiving notch 216 and valve-receiving slots 218. Similar to valve 196 (FIG. 9A), valve 212 includes a valve body 220 and ribs 222. Ribs 222 are sized to mate within valve-receiving slots 218 of horn 208. In this regard, valve-receiving slots 218 are positioned proximate a proximal end 224 of horn 208. Introducer 206, including valve 212, functions in a manner highly similar to introducer 190 (FIG. 9A) as previously described.

It is recognized that the fluid blocking function provided by valve 212 can be achieved with other designs. For example, referring to FIG. 9C, an alternative embodiment of an introducer 226 is shown. Introducer 226 includes a horn 228, a neck 230 and an O-ring 232. Horn 228 and neck 230 are preferably formed as an integral body. Horn 228 preferably includes a guidewire-receiving notch (not shown) similar to that previously described and an interior slot 234. Interior slot 234 is preferably positioned proximate neck 230 and is sized to maintain O-ring 232. Alternatively, interior slot 234 can be formed in neck 230. O-ring 232 is preferably made of a rubber-type material. Further, O-ring 232 has an inner diameter slightly smaller than that of horn 228 and neck 230. Thus, during use, O-ring 232 forms a seal about catheter shaft 38 (FIG. 1), blocking passage of bodily fluids, such as bile, into horn 228.

Figure 9F:
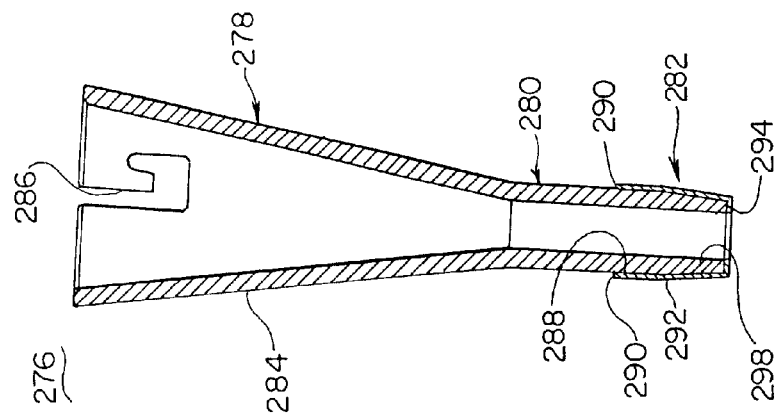
FIG. 9F is an enlarged, cross-sectional view of another alternative embodiment of the introducer of FIG. 8.
Figure 9E:
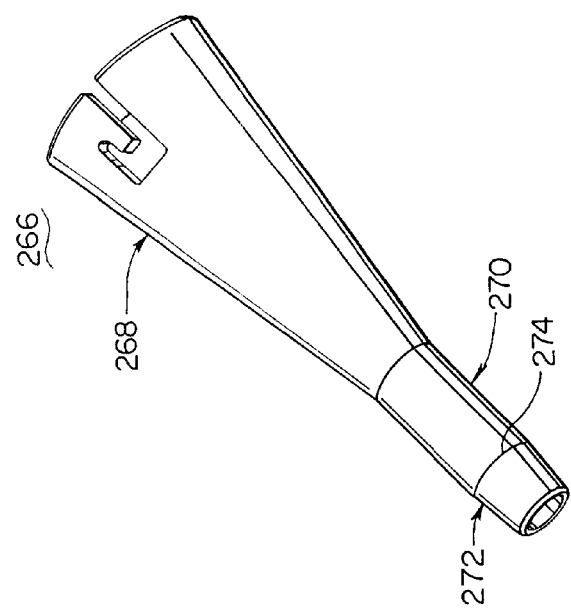
FIG. 9E is an enlarged, perspective view of another alternative embodiment of the introducer of FIG. 8.
Figure 9D:
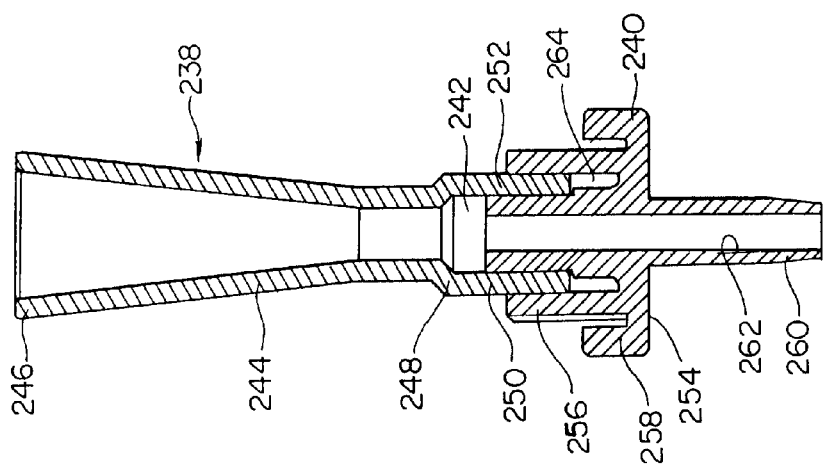
FIG. 9D is an enlarged, cross-sectional view of another alternative embodiment of the introducer of FIG. 8.

Referring to FIG. 9D, another alternative embodiment of an introducer 236 is shown. Introducer 236 is similar to a touhey-borst system and includes an upper horn section 238, a lower horn section 240 and a grommet 242. Upper horn section 238 includes an outer wall 244 defining a proximal end 246, a grommet-receiving flange 248 and a distal end 250. Proximal end 246 of horn section 238 preferably includes a guidewire-receiving notch (not shown) similar to that previously described. Distal end 250 is threaded and includes a passage 252 sized to receive a portion of lower horn section 240.

Lower horn section 240 includes a body 254 defining a proximal end 256, an intermediate portion 258 and a distal end 260. An interior passage 266 is configured to communicate with passage 252 and extends from proximal end 256 to distal end 260. Finally, proximal end 256 includes a threaded slot 262 sized to threadably receive distal end 250 of upper horn section 238.

Grommet 242 is preferably made of a rubber-type material and is sized to nest within grommet-receiving flange 248 of upper horn section 238 while abutting proximal end 256 of lower horn section 240.

Introducer 236 is assembled by placing grommet 242 within grommet-receiving flange 248 of upper horn section 238. Distal end 250 of upper horn section 238 is then threadably secured to proximal end 258 of lower horn section 240. As upper horn section 238 is threadably secured to lower horn section 240, proximal end 256 of lower horn section 240 compresses grommet 242 within grommet-receiving flange 248 of upper horn section 238. During use, introducer 236 functions in a manner highly similar to that previously described. In this regard, grommet 242 forms a seal about catheter shaft 38 (FIG. 1). Further, aspiration can be achieved, if desired, by loosening lower horn section 240 relative to upper horn section 238.

Referring to FIG. 9E, yet another alternative embodiment of an introducer 266 is shown. Introducer 266 includes a horn 268, a neck 270 and a valve 272. Preferably, horn 268, neck 270 and valve 272 are integrally formed as a singular body. In this regard, valve 272 is formed while molding horn 268 and neck 270 by imparting a controlled flash at distal end 274 of neck 270.

Introducer 266 performs in a manner highly similar to that previously described. Thus, valve 272 forms a seal about catheter shaft 38 (FIG. 1), thereby preventing back flow of bodily fluids, such as bile, into horn 268.

Referring to FIG. 9F, another alternative embodiment of an introducer 276 is shown. Introducer 276 includes a horn 278, a neck 280 and a valve 282. Horn 278 and neck 280 are preferably integrally formed as a singular body. In this regard, horn 278 and neck 280 are defined by an outer wall 284. Outer wall 284 forms a guidewire-receiving notch 286 and an exterior slot 288. Guidewire-receiving notch 286 is similar to that previously described. Exterior slot 288 is positioned along neck 280 and is sized to maintain a portion of valve 282. Alternatively, exterior slot 288 can be positioned along horn 278.

Valve 282 is preferably a rubber-type sock defined by an upper rib 290, a sidewall 292 and a shoulder 294. Upper rib 290 is preferably sized to mount within exterior slot 288 of neck 280. Sidewall 292 is preferably flexible so as to stretch along neck 280. Finally, shoulder 294 is preferably configured to abut a distal end 298 of neck 280. With this configuration, valve 282 is placed over distal end 298 of neck 280 such that shoulder 294 contacts distal end 298. Due to the preferred flexible characteristic of valve 282, side wall 292 is stretched until upper rib 290 nests within exterior slot 288 of neck 280.

During use, the catheter shaft 38 (FIG. 1) is placed through introducer 276 such that shoulder 294 of valve 282 forms a seal about catheter shaft 38. Thus, valve 282 prevents undesired back flow of bodily fluids, such as bile.

Figure 10:
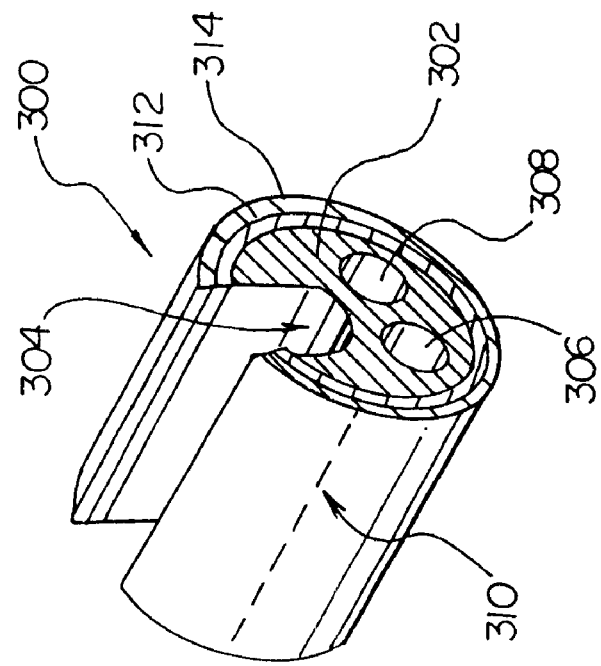
FIG. 10 is an enlarged fragmentary perspective view of a multi-size convertible catheter section which defines the shaft of an alternative embodiment of the catheter of FIG. 1.

Referring to FIG. 10, a section of a multi-size convertible catheter is shown. The multi-size catheter assembly is preferably the same as that described in FIG. 1, except for the shaft construction detailed herein. The catheter includes a catheter hub assembly and a multi-size catheter 300, having a guidewire passing through a portion thereof. The variation between the assembly of FIG. 1 and FIG. 10 is the inclusion of a multi-size catheter 300 in place of the catheter 34. Multi-size catheter 300 similarly incorporates features that allow rapid exchange of the catheter by a single operator. This feature, as well as others discussed in detail below, allows multi-size catheter 300 to be used in a variety of medical procedures. The multi-size catheter 300 may especially be used in conjunction with urinary, biliary, and vascular procedures. Among the more frequent uses envisioned for multi-size catheter 300, however, is in catheter procedures for accessing targeted anatomical regions through the alimentary canal via an endoscope.

FIG. 10 illustrates a section of multi-size catheter 300 depicting co-axially disposed peelable layers situated upon a catheter shaft 302 with subsequent layers overlaying previous layers. Multi-size catheter 300 includes the shaft 302, which in general terms has a proximal end, a U-channel 304, a distal tip region, a distal end, and various lumens 306 and 308. Multi-size catheter 300 further includes at least one peelable layer disposed about the exterior of catheter shaft 302. A predisposed line of weakness 310 may be included into the polymeric layer. This line of weakness 310 extends longitudinally along the peelable layer. In a preferred embodiment, the line of weakness 310 is a perforated line located diametrically opposite U-channel 304. In an alternate embodiment, two diametrically opposed lines of weakness may be incorporated into the peelable layer.

Two peelable layers 312 and 314 are illustrated in FIG. 10. Peelable layer 312 is removably attached to the exterior of catheter shaft 302. In a preferred embodiment, peelable layer 312 is removably affixed to catheter shaft 302 along the catheter shaft's entire length except in those areas forming U-channel 304. Peelable layer 314 is similarly attached to peelable layer 312. Peelable layer 314 defines a first diameter for multi-size catheter 300. Peelable layer 312 defines a second diameter for multi-size catheter 300 being less than that defined by peelable layer 314. Therefore, when peelable layer 314 is removed from multi-size catheter 300, peelable layer 312 subsequently defines a reduced outer diameter for multi-size catheter 300. In an additional embodiment, tabs, or other appendages denoting individual peelable layers, may be placed at the proximal end of the multi-size catheter 300. These tabs allow a physician to readily remove either a single layer, or a group of layers. Each tab may additionally be color-coded to indicate their resultant outer diameter circumference. This is especially useful when the inner diameter for an endoscope is known. With this system, a physician must merely remove all peelable layers above the corresponding outer diameter tab that matches the inner diameter for the endoscope.

Between one and ten peelable layers are used to vary the outer diameter of multi-size catheter 300. Preferably, two to five peelable layers are superimposed upon one another in order to achieve the desired outer diameter. Each peelable layer is approximately 0.4 mm in thickness. The peelable layers, however, may range in thickness between 0.1 mm to 0.7 mm. Furthermore, peelable layers 310 and 312 are generally formed from an extruded polymeric material. In one embodiment, the preferred polymeric material is polyether block amide, polytetrafluoroethylene, nylon, or a combination or blend of these. Additional polymers suitable for forming peelable layer include polyethylene, various co-polymers and blends of polyethylene, polyesters, polyurethanes, polyamides, and the mixtures thereof. In a further embodiment, the peelable layers may include a highly lubricious coating. This coating may be disposed either upon the exterior of the layer, or incorporated therein.

Figure 11:
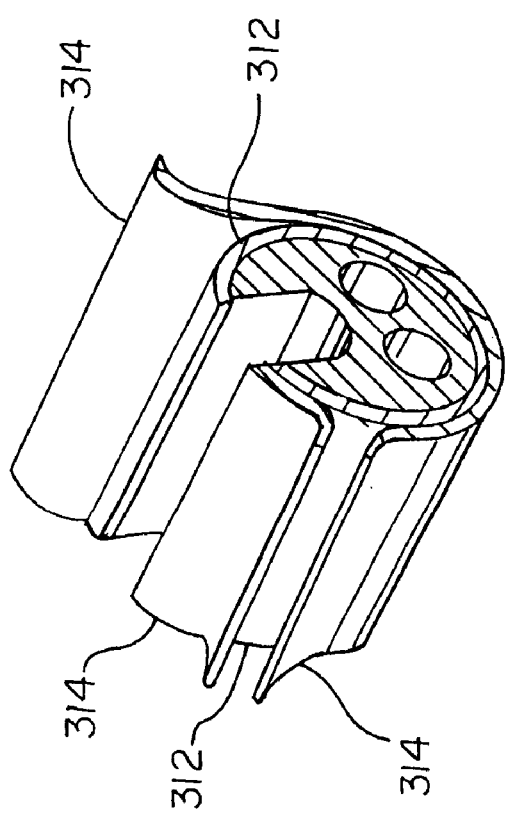
FIG. 11 is an enlarged fragmentary perspective view of a peelable layer being removed from the multi-size convertible catheter of FIG. 10.

Referring to FIG. 11, peelable layer 314 is shown being removed from multi-size catheter 300. Peelable layer 314 is being removed from both a line of weakness formed on the top, and from the side, of the multi-sized catheter. In order to facilitate the removal of peelable layer 314, a slit may be made along the predisposed line of weakness 310. This slit may be made by ordinary means known in the art. Once the slit is made, the peelable layer may be removed from either direction.

Referring to FIGS. 12A through 12D, cross-sectional views of endoscope working channels 70–76 containing a multi-size catheter 300 are shown. Each view illustrates multi-size catheter 300 having peelable layers selectively removed to afford the best fit within the working channel of the endoscope. The advantages of multi-size catheter 300 are best observed in conjunction with FIGS. 2A–2D depicting catheter 34. In the examples illustrated in FIGS. 2A–2D and 12A–12D, working channel inside diameters 70, 72, 74, and 76 are 2.8, 3.2, 3.8, and 4.2 mm, respectively.

Figure 12A:
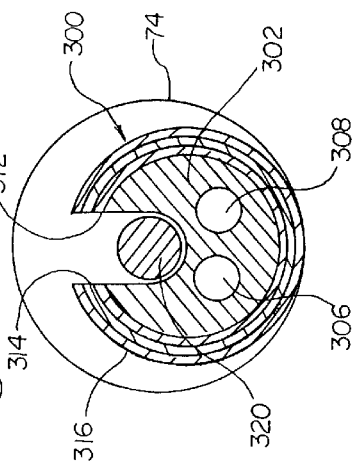
FIGS. 12A–12D are cross-sectional views of the multi-sized convertible catheter adapted for use within increasingly larger endoscope channels.

FIG. 12A illustrates multi-size catheter 300 having catheter shaft 302, ancillary lumens 306 and 308, U-channel 304, guidewire 320, and four peelable layers 312, 314, 316, and 318 within endoscope working channel 76. In FIG. 12A, guidewire 320 is effectively radially constrained within working channel 76. The depth of U-channel 304 is extended by peelable layers 312, 314, 316, and 318. Therefore, guidewire movement is constrained to within U-channel 304 only. The guidewire 320 is effectively stopped from slipping out of U-channel 304, thereby eliminating the potential for guidewire 320 to become pinched and restrict desired movements of both the guidewire 320 and catheter 300. FIG. 2D illustrates how the guidewire 36 may exit U-channel 42 and become pinched within the identically sized endoscopic working channel 76. An exchange sheath would be necessary to constrain guidewire movement to within U-channel 42 for catheter 34 in FIG. 2D. This involves inserting an exchange sheath within the endoscope, and then placing catheter 34 within the exchange sheath. Furthermore, multiple exchange sheaths of varying sizes are needed on hand to match the outer diameter of the catheter to the inner diameter of the desired endoscope. This is both time consuming and costly because it requires this second device. Multi-size catheter 300, however, achieves the same desired effect in a single medical device. An exchange sheath is unnecessary with multi-size catheter 300 because peelable layers 312, 314, 316, and 318, more or less as needed, provide radial constrainment of the catheter within various sized working channels.

Figure 12B:
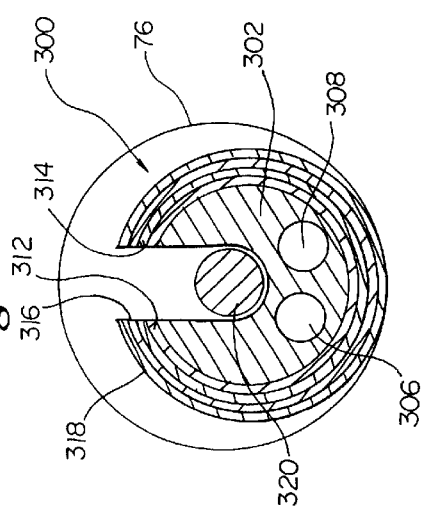

FIG. 12B illustrates multi-size catheter 300 having three peelable layers 312, 314, and 316 within a smaller endoscope working channel 74. This multi-size catheter 300 may come with three peelable layers, or at least one peelable layer may have been removed to correctly size multi-size catheter 300 for working channel 74. The three peelable layers 312, 314, and 316 of multi-size catheter 300 sufficiently constrain all guidewire movement to within U-channel 304 in endoscope 74. In the identically sized working channel 74 in FIG. 2C, catheter 34 is again capable of slipping out of U-channel 42 and becoming pinched.

Figure 12C:
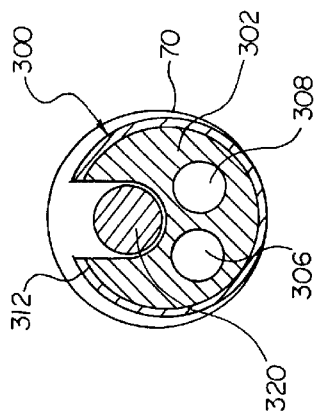
Figure 12D:
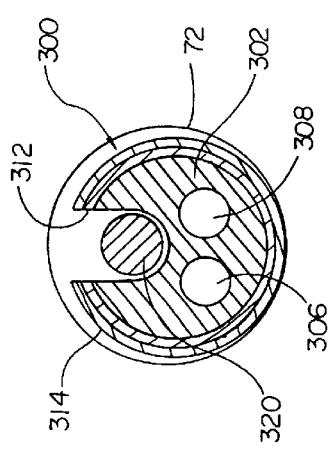

FIG. 12C illustrates multi-size catheter 300 having two peelable layers 312 and 314 within an even smaller endoscope working channel 72. FIG. 12D illustrates multi-size catheter 300 having one peelable layer 312 within the smallest described endoscope working channel 70. These multi-size catheters 300 may, again, come with only the described number of peelable layers, or at least one peelable layer may have been removed from to correctly size these catheters within their corresponding endoscope channels. Referring to FIG. 12D specifically, the tolerance between endoscope working channel 70 and peelable layer 312 of multi-size catheter 300 is tighter than between catheter shaft 38 and endoscope working channel 70 in FIG. 2A. Tighter tolerances coincide with better trackability and pushability within the working channel of the endoscope.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims. For example, while the rapid exchange catheters of the present invention have been preferably described as being biliary catheters, other applications are also envisioned. Thus, the catheters of the present invention can be used with biopsy, metal stent placement, plastic stent placement, snares, baskets, etc. Additionally, the catheters of the present invention may have vascular applications, where a guide catheter is substituted for the endoscope to constrain the guidewire.

What is claimed is:

1. A multi-size catheter having an adjustable outer diameter, the catheter comprising:
    a catheter shaft having a proximal end, a distal end, and a guidewire lumen extending longitudinally therethrough; and
    at least one peelable layer superimposed over the catheter shaft and releasably affixed to the catheter shaft, the at least one peelable layer defining a first catheter diameter;
    wherein removing the at least one peelable layer provides a catheter having a second catheter diameter that is less than the first catheter diameter.

2. The multi-size catheter of claim 1, wherein the catheter is a biliary catheter.

3. The multi-size catheter of claim 1, wherein the catheter is a single operator exchange catheter having a channel for accessing the guidewire lumen from a location exterior to the catheter shaft.

4. The multi-size catheter of claim 1, wherein the at least one peelable layer has a thickness of 0.4 mm or less.

5. The multi-size catheter of claim 1, wherein the catheter comprises two peelable layers.

6. The multi-size catheter of claim 1, wherein the catheter comprises three peelable layers.

7. The multi-size catheter of claim 1, wherein the catheter comprises four peelable layers.

8. The multi-size catheter of claim 1, wherein the catheter comprises five peelable layers.

9. The multi-size catheter of claim 1, wherein the at least one peelable layer is a polymeric material selected from the group consisting of polyethylene, various co-polymers and blends of polyethylene, PTFE, polyethylene block amide, polyesters, polyurethanes, polyamides, nylon, and mixtures thereof.

10. The multi-size catheter of claim 1, wherein the at least one peelable layer includes a highly lubricious coating disposed thereon or therein.

11. A catheter having an adjustable outer diameter, the catheter comprising:
    a catheter shaft having a proximal end, a distal end, and a guidewire lumen extending longitudinally therethrough;
    at least one peelable layer, having a proximal end and a distal end, the peelable layer superimposed over the catheter shaft wherein the outermost peelable layer defines a first outer diameter of the catheter; and
    a means for removing the peelable layer superimposed over the catheter shaft;

wherein removing the at least one peelable layer provides a catheter having a second outer diameter that is less than the first outer diameter.

12. The catheter of claim 11, wherein the catheter is a single operator exchange catheter.

13. The catheter of claim 11, wherein the removing means is at least one line of weakness extending longitudinally along the peelable layer, whereby the peelable layer may be torn along the at least one line of weakness, thereby removing the peelable layer from the catheter.

14. The catheter of claim 13, wherein the at least one line of weakness includes two diametrically opposed perforated lines, the perforated lines extending longitudinally along the peelable layer.

15. A biliary catheter comprising:
   a catheter shaft having a proximal end, a distal end, and a guidewire lumen extending longitudinally therethrough; and
   at least one peelable layer extending the length of, and superimposed upon, the catheter shaft, wherein the outermost peelable layer defines a first outer diameter of the catheter and removing the outermost peelable layer provides a biliary catheter having a second outer diameter that is less than the first outer diameter.

16. The biliary catheter of claim 15, wherein the catheter shaft includes a channel for accessing the guidewire lumen from a location exterior to the catheter shaft, the channel extending longitudinally along a portion of the catheter shaft.

17. The biliary catheter of claim 15, the peelable layer comprises at least one line of weakness extending longitudinally along the peelable layer, whereby the peelable layer may be torn along the at least one line of weakness, thereby removing the peelable layer from the catheter.

18. The catheter of claim 17, wherein the at least one line of weakness includes two diametrically opposed perforated lines, the perforated lines extending longitudinally along the peelable layer.

19. In a biliary single operator exchange catheter for use with an endoscope having a working channel with an inner diameter, the biliary catheter comprising:
   a catheter shaft having a proximal end, a distal end, and an exterior wall;
   a guidewire lumen extending longitudinally therethrough the catheter shaft between a location proximate the distal end of the shaft and a location proximal of the distal end of the shaft;
   at least a part of the exterior wall of the shaft defining a channel, the channel being in communication with the guide wire lumen; and
   at least one peelable layer superimposed over the catheter shaft defining a first outer diameter of the catheter;
   wherein removing the at least one peelable layer provides a catheter having a second outer diameter that is less than the first outer diameter.

20. The biliary catheter of claim 19, wherein the at least one peelable layer does not superimpose over the channel.

21. The biliary catheter of claim 19, wherein the at least one peelable layer is removable.

22. The biliary catheter of claim 19, wherein the peelable layer comprises of at least one line of weakness extending longitudinally along the peelable layer, whereby the peelable layer may be torn along the at least one line of weakness, thereby removing the peelable layer from the catheter.

23. The biliary catheter of claim 19, wherein the outer diameter of the catheter is less than, but approximate to, the inner diameter of the working channel of the endoscope.

24. The biliary catheter of claim 19, wherein the at least one peelable layer has a thickness of 0.4 mm or less.

25. The biliary catheter of claim 19, wherein the catheter comprises two peelable layers.

26. The biliary catheter of claim 19, wherein the catheter comprises three peelable layers.

27. The biliary catheter of claim 19, wherein the catheter comprises four peelable layers.

28. The biliary catheter of claim 19, wherein the catheter comprises five peelable layers.

29. The biliary catheter of claim 19, wherein the at least one peelable layer is a polymeric material selected from the group consisting of polyethylene, various co-polymers and blends of polyethylene, PTFE, polyethylene block amide, polyesters, polyurethanes, polyamides, nylon, and mixtures thereof.

30. The biliary catheter of claim 19, wherein the at least one peelable layer includes a highly lubricious coating disposed thereon or therein.

* * * * *

UNITED STATES PATENT AND TRADEMARK OFFICE
CERTIFICATE OF CORRECTION

PATENT NO.    : 6,582,401 B1
DATED         : June 24, 2003
INVENTOR(S)   : James E. Windheuser et al.

It is certified that error appears in the above-identified patent and that said Letters Patent is hereby corrected as shown below:

Column 6,
Line 6, delete "cm", and insert therefor -- an --.
Line 40, delete "medical-procedure", and insert therefor -- medical procedure --.

Column 9,
Line 35, delete "arid", and insert therefor -- and --.

Column 11,
Line 62, delete "out-of", and insert therefor -- out of --.

Column 17,
Line 30, after "of claim 15", insert -- wherein --.

Signed and Sealed this

Thirteenth Day of July, 2004

JON W. DUDAS
*Acting Director of the United States Patent and Trademark Office*